United States Patent
Colombo et al.

(10) Patent No.: US 6,495,534 B2
(45) Date of Patent: Dec. 17, 2002

(54) STABILIZED AQUEOUS SUSPENSIONS FOR PARENTERAL USE

(75) Inventors: Giuseppe Colombo, Milan (IT); Alessandro Martini, Milan (IT); Lloyd E. Fox, Richland, MI (US)

(73) Assignees: Pharmacia & Upjohn SpA, Milan (IT); Pharmacia & Upjohn Company, Kalamazoo, MI (US)

( * ) Notice: Subject to any disclaimer, the term of this patent is extended or adjusted under 35 U.S.C. 154(b) by 0 days.

(21) Appl. No.: 09/571,395

(22) Filed: May 15, 2000

(65) Prior Publication Data

US 2002/0115645 A1 Aug. 22, 2002

(51) Int. Cl.⁷ ................................ A61K 31/56
(52) U.S. Cl. ................ 514/169; 514/178; 514/182
(58) Field of Search ................. 514/169, 178, 514/182

(56) References Cited

U.S. PATENT DOCUMENTS

| | | | |
|---|---|---|---|
| 4,154,820 A | * 5/1979 | Simoons | 424/175 |
| 5,569,464 A | 10/1996 | Endo et al. | |
| 5,773,432 A | * 6/1998 | Kauser et al. | 514/182 |
| 5,846,962 A | * 12/1998 | Suzuki et al | 514/177 |
| 5,880,116 A | * 3/1999 | Vigo-Pelfrey | 514/178 |
| 5,916,550 A | 6/1999 | Inada et al. | |
| 5,972,921 A | * 10/1999 | Santti et al. | 514/177 |
| 6,040,301 A | 3/2000 | Skrabanja et al. | |
| 6,114,324 A | 9/2000 | Skrabanja et al. | |

FOREIGN PATENT DOCUMENTS

| | | |
|---|---|---|
| CA | 2304808 | 4/1999 |
| EP | 0431663 | 6/1991 |
| EP | 0 868 919 A | 10/1998 |
| JP | 63 146829 A | 6/1988 |
| JP | 05 097671 A | 4/1993 |
| JP | 08 245421 A | 9/1996 |
| JP | 10-212303 | 8/1998 |
| WO | WO 98 11912 A | 3/1998 |
| WO | 98/14476 * | 4/1998 |
| WO | WO 98/14476 | 4/1998 |
| WO | WO 99 15193 A | 4/1999 |
| WO | WO99/51237 | 10/1999 |
| WO | WO 01 24814 A | 4/2001 |

OTHER PUBLICATIONS

Merck Index, ninth edition, 1976, 3629 & 5618, 1976.*
The Merck Index, 12th Edition, 1996, p. 1023.

* cited by examiner

Primary Examiner—Barbara P. Badio
(74) Attorney, Agent, or Firm—Oblon, Spivak, McClelland, Maier & Neustadt, P.C.

(57) ABSTRACT

A pharmaceutical aqueous suspension formulation for parenteral administration having substantially stabilized pH, comprising a biologically active compound and a pH controlling effective concentration of L-Methionine.

Preferably, the biologically active compound is a steroidal compound, for instance exemestane, medroxyprogesterone acetate and estradiol cypionate or a combination of medroxyprogesterone acetate and estradiol cypionate.

21 Claims, No Drawings

STABILIZED AQUEOUS SUSPENSIONS FOR PARENTERAL USE

SUMMARY OF THE INVENTION

The present invention is in the field of galenic preparations. It concerns in particular a pharmaceutical aqueous suspension of a biologically active compound, e.g. a steroidal compound, having stabilized pH, particularly suitable for parenteral administration.

The inventors of the present invention have found that the pH of a pharmaceutical aqueous suspension of a biologically active compound can be controlled by adding a pH controlling effective concentration of L-Methionine thereto.

Moreover, when a pH controlling effective concentration of L-Methionine is used, it strengthens the buffering capacity of low concentrations of conventional buffering agents with a super-additive (synergistic) effect. In this way the use of conventional buffering agents can be eliminated or limited, thus improving the re-suspendability and controlled flocculation of the pharmaceutical preparation.

BACKGROUND OF THE INVENTION

A pharmaceutical suspension is a coarse dispersion in which insoluble solid particles are dispersed in a liquid medium.

Suspensions contribute to pharmacy and medicine by supplying insoluble and often distasteful substances in a form that is pleasant to the taste, by providing a suitable form for the application of dermatological materials to the skin and sometimes to the mucous membranes, and for the parenteral administration of insoluble drugs. Therefore pharmaceutical suspensions may be classified into three groups: orally administered mixtures, externally applied lotions and injectable preparations.

An acceptable suspension possesses certain desirable qualities, including the followings:
i) the suspended material should not settle rapidly;
ii) the particles that do settle to the bottom of the container must not form a hard cake but should be readily re-dispersed into a uniform mixture when the container is shaken;
iii) the suspension must not be too viscous to pour freely from the orifice of the bottle or to flow through a syringe needle.

It is important that the characteristics of the dispersed phase are chosen with care so to as to produce a suspension having optimum physical, chemical and pharmacological properties. Particle size distribution, specific surface area, inhibition of crystal growth, and changes in the polymorphic form are of special significance and the formulator must ensure that these and other properties do not change sufficiently during storage to adversely affect the performance of the suspensions with aging.

In the field of injectable preparations, aqueous suspensions for parenteral administration have already been described in scientific and patent literature and have been known for a long time. Parenteral suspensions are often prepared with the so called "controlled flocculation" approach, i.e. by the application of known principles of formulation chemistry to produce vehicles which permits drug flocs to form and settle, but which they are easily re-suspended with slight agitation and remain uniformly dispersed or suspended during the period required for therapeutic administration. Specifically, it is well known that one of the main difficulty in formulating parenteral aqueous suspensions of steroids is the overcome of their hydrophobicity, that significantly reduce the wettability, suspendability or re-suspendibility of the active in aqueous media. Both wetting and suspending agents are needed in order to gain the proper formulation of the active compound such as the concomitant use of preservatives. This is described, for example, by Nash and coworkers in the U.S. Pat. No. 3,457,348 where non-ionic surfactants (such as polysorbates) and suspending agents (like polyethylene glycols) are the basic excipients to gain the proper stability of the formulation.

Sometimes, even in the presence of the proper suspending and wetting agents, the suspension is not stable for a long time, but it is necessary to form it just before the administration (while it is stored as lyophilized formulation). This is described, for example, in the case described by Geller and coworkers in the U.S. Pat. No. 5,002,940 and greatly impacts on the cost of the manufacturing process, since an additional freeze-drying process is mandatory.

Even if an improved physical stability of steroidal drug suspensions in water can be gained, as above mentioned, by the use of polyethylene glycols and non-ionic surfactants, some chemical stability issues, such as a relevant pH reduction, are likely to be faced during development.

In fact, for instance, both polyethylene glycols and polysorbates, when in solution, may undergo degradation, leading to the formation of acid species such as formic and acetic acid.

An example of this pH reduction effect is given in Table 1.

TABLE 1 pH of a typical vehicle for parenteral aqueous suspensions formulations Vehicle composition (batch 13169/12-1A): Methylparaben 0.2%, propylparaben 0.02%, sodium chloride 0.9%, PEG 4000 3%, polysorbate 80 0.3%, sodium hydroxide q.s. to pH 6.5 , WH q.s to 100 ml.

| Storage condition | PH |
|---|---|
| Time zero | 6.46 |
| 10 days at 65° C. | 3.43 |
| 15 days at 65° C. | 3.16 |
| 1 month at 65° C. | 3.32 |
| 3 months at 40° C. | 3.24 |
| 6 months at 40° C. | 3.15 |
| 6 months at 25° C. | 4.93 |

This pH reduction occurs both at accelerated testing conditions and at room temperature. Considering that after only 6 months at room temperature a relevant decrease of approximately 1.5 pH unit is experimented, very low pH values (close or below 3) are anticipated after long-term storage (1–2 years). This fact necessarily causes the reduced shelf life of parenteral suspension, being the progressive acidification of the formulation linked to the impossibility to administer the formulation, e.g. by intramuscular or subcutaneous injection, without generating significant pain on patients (it is advisable that the pH value is maintained above 3 for administering a painless formulation).

This pH variation during storage can be minimized by appropriately buffering the formulation. The most obvious approach, in order to maintain the pH within specific and predetermined limits, is the use of buffering agents, such as inorganic acid salts, in appropriate concentrations in order not only to exert but also to maintain their buffering capacity. An example of buffering agents commonly used in parenteral formulations and of their usual concentrations can be found in Pharmaceutical Dosage Form: Parenteral Medications, Volume 1, $2^{nd}$ Edition, Chapter 5, p. 194, De Luca and Boylan, "Formulation of Small Volume Parenterals", Table 5: Commonly used additives in Parenteral Products The use of inorganic acid salts as buffering agents offers to the formulator both advantages and disadvantages. In fact, if a careful control of pH of formulations could be gained, on the contrary, when suspension formulations are concerned, ionic species tend to destabilize the formulations with detrimental effects on the re-suspendability and on the controlled flocculation of the formulation. This means that the use of inorganic acid salt based buffering systems into the formulations has to be minimized.

In fact, when talking about parenteral suspension, according to Nash (Parenteral Suspensions, Bulletin of Parenteral Drug Association, March–April 1972, Vol. 26, No. 2), ". . . indiscriminate use of salts and buffers is normally avoided, provided chemical stability is not a problem since changes in electrolyte concentration often have a profound effect on the absorbed surface charge of suspension particles".

An example of the relevant pH decrease occurring in a medroxyprogesterone acetate parenteral aqueous suspension is showed in Table 2. This accelerated stability study shows that the pH of an unbuffered formulation significantly decrease from an initial pH value of approx. 6.5 to pH values of 3 or lower than 3. It also demonstrates that, when a usual concentration (approx. 1%) of phosphate buffer is added to control the pH, a detrimental effect on the suspension re-suspendability and syringeability is experimented. In fact an increased time of manual wrist shaking is needed to re-suspend the buffered suspension after 1 month at 55° C. vs. the unbuffered one. Besides, after 2 month at 55° C. the buffered suspension cannot be re-suspended at all by manual wrist shaking and, as a consequence, cannot be administered. On the other hand, when a lower and unusual concentration (approx. 0.1%) of phosphate buffer is used, no relevant effect on suspension re-suspendability is experimented but, at the same time, no substantial pH control is obtained.

TABLE 2 pH, re-suspendability and syringeability study of "buffered" vs. "as is" 20% Medroxy ProgesteroneAcetate parenteral aqueous suspension formulations
Suspension composition (batch 13451/01-1): Medroxyprogesterone acetate 20%, MyristylGammaPicoliniumChloride 0.2%, sodium sulphate 1.1%, PEG 3350 2.03%, sodium hydroxide q.s. to pH 6.5, WFI q.s to 100 ml.

| | 13451/01-1 | | | | | | | | |
|---|---|---|---|---|---|---|---|---|---|
| | A: as is | | | B: + Phosphate buffer ~0.1% | | | C: Phosphate buffer ~1% | | |
| Batch | pH | Syring. | pH | Resusp. | Syring. | PH | Resusp. | Syring. |
| Time zero | 6.35 | R (T = 7 s) | MT | 6.71 | R (T = 8 s) | MT | 6.30 | R (T = 10 s) | MT |
| 1 month at 55° C. | 3.12 | R (T = 18 s) | MT | 3.67 | R (T = 29 s) | MT | 5.94 | R (T = 40 s) | MT |
| 2 months at 55° C. | 2.92 | R (T = 33 s) | MT | 3.28 | R (T = 24 s) | MT | 5.93 | NR | NP |
| 3 months at 55° C. | 2.83 | R (T = 31 s) | MT | 3.15 | R (T = 32 s) | MT | 5.81 | NR | NP |
| Phosphate Buffers (M = molar) | | | | Concentration ~0.1% | | | Concentration ~1% | | |
| Monobasic Sodium Phosphate.1 H2O (MW 137.99) | | | | mg 69.4/100 ml (0.005M) | | | mg 694/100 ml (0.05M) | | |
| Dibasic Sodium Phosphate.12 H2O (MW 358.14) | | | | mg 58.8/100 ml (0.0016M) | | | mg 588/100 ml (0.016M) | | |

Resuspendability
R = RESUSPENDABLE by manual wrist shaking. In brackets: T = time of manual wrist shaking requested in order to obtain a homogeneous suspension (s = seconds).
NR = NOT RESUSPENDABLE
Syringeability
MT = meets test
NP = not performed as product cannot be resuspended and therefore cannot be homogeneously withdrawn and syringed

DESCRIPTION OF THE INVENTION

The inventors of the present invention have surprisingly found out that suitable concentrations of L-Methionine are able both to control the pH of a pharmaceutical aqueous suspension of a biologically active compound, in particular a steroidal compound, by minimizing its pH decrease and to strengthen the pH controlling capacity of lower and unusual concentrations of conventional buffering agents, with a super-additive (synergistic) effect.

In fact the gist of the present invention is based on the finding that an oxygen scavenger such as L-Methionine not only shows antioxidant properties per se, like known antioxidant thiol-derivatives, but surprisingly itself takes part in pH controlling activity.

A first object of the present invention is thus to provide the use of L-Methionine as pH controlling agent in a pharmaceutical aqueous suspension formulation having substantially stabilized pH, for parenteral administration of a biologically active compound.

A further object of the present invention is to provide a pharmaceutical aqueous suspension formulation for parenteral administration having substantially stabilized pH comprising a biologically active compound and a pH controlling effective concentration of L-Methionine.

Object of the invention is also the use of L-Methionine, in a pH controlling effective concentration, in the preparation of a pharmaceutical aqueous suspension formulation having substantially stabilized pH, for parenteral administration of a biologically active compound.

A further object is a method for preparing a pharmaceutical aqueous suspension formulation for parenteral administration of a biologically active compound having substantially stabilized pH, characterized in that a pH controlling effective concentration of L-Methionine is added thereto.

The inventors have also found that L-Methionine, besides exercising a pH controlling activity per se, also strengthens the pH controlling capacity of a conventional buffer with a (super-additive) synergistic effect.

A super-additive (synergistic) effect is a pH controlling effect that is greater than the one which is expected to be obtainable by summing up the experimentally verified pH controlling effects of the single agents.

This means that low unusual concentrations of conventional buffering agents can be included into the formulations, without any risk of loosing in buffering capacity and, at the same time, to deteriorate the physico-technological quality of parenteral suspensions.

A further advantage is given by the fact that as no relevant concentrations of buffers are needed, the formulation has low or no buffering capacity per se and therefore, once administered, the pH of the formulation will be easily adjusted to the physiological value by the buffering capacity of body fluids.

As stated above, the reduction in the quantity of conventional buffering agents, such as inorganic acid salts, improves the physical stability of the formulation, since ionic species tend to destabilize the formulations with detrimental effects on the re-suspendibility and on the controlled flocculation of the formulation.

A further object of the invention is therefore to provide a pharmaceutical aqueous suspension formulation for parenteral administration having substantially stabilized pH comprising a biologically active compound, a buffering agent and L-Methionine in concentrations effective to produce a pH controlling super-additive effect.

The present invention also provides the combined use of L-Methionine and a conventional buffering agent in concentrations effective to produce a pH controlling super-additive effect, in the preparation of a pharmaceutical aqueous suspension formulation having substantially stabilized pH, for parenteral administration of a biologically active compound.

The term "a buffering agent" is herein meant to comprise (unless otherwise specified) both a single buffering agent and a mixture of two or more thereof.

The term "substantially pH stabilized" means that the pH of the formulation remains within acceptable limits for parenteral administration over the time, according to well known practice in the art. It also means that the pH of the formulation containing L-Methionine, or the combination of L-Methionine and a buffering agent in concentrations effective to provide a pH controlling super-additive effect, is maintained over the time closer to the initial value than the pH of the "as is" formulation (i.e. the formulation without L-Methionine or the combination of L-Methionine and a buffering agent).

The pH range for the suspension formulation of the invention is from about pH 3.0 to about pH 8.0, preferably pH 3.0 to pH 7.5, and most preferably pH 4.0 to pH 7.0.

A pH controlling effective concentration of L-Methionine, when used as a single pH controlling agent, may vary from about 0.005% w/v to about 5% w/v, preferably from about 0.01% w/v to about 1.0% w/v.

The pH controlling effective concentration of L-Methionine, when used as a combined pH controlling agent, may be substantially the same as above.

Thanks to the pH controlling properties of L-Methionine and the superadditive pH controlling effect, which is obtainable by using L-Methionine in combination with a conventional buffering agent, the concentration of the latter can be reduced by about 50% to about 95%. Namely the concentration of the buffering agent can thus range from about 5% to about 50% of the usual buffering concentration thereof, preferably from about 5% to about 25%.

The usual concentrations of conventional buffering agents employed in parenteral formulations can be found in: Pharmaceutical Dosage Form: Parenteral Medications, Volume 1, $2^{nd}$ Edition, Chapter 5, p. 194, De Luca and Boylan, "Formulation of Small Volume Parenterals", Table 5: Commonly used additives in Parenteral Products.

According to said literature, the usual buffering concentration for phosphoric acid salts range from about 0.8% to about 2.0% w/v or w/w. On the contrary, thanks to the newly found super-additive effect, the concentration of phosphoric acid salts according to the formulation of the invention are lower than 0.4% w/w or w/v, preferably lower than 0.2% w/w or w/v.

Re-suspendibility and controlled flocculation of the pharmaceutical aqueous suspension are thus improved.

The pharmaceutical aqueous suspension, according to the invention, may in addition also include one or more surfactants, suspending agents and/or thickening agents.

Suitable surfactants are for instance phospholipids (e.g. lecithin), cationic surfactants (e.g. myristylgammapicolinium chloride), anionic surfactants and non-ionic surfactants (e.g. polysorbate 80).

Suitable suspending and/or density adjusting agents are for instance polyvinylpyrrolidone compounds and polyethylene glycols. Preferred examples of polyethylene glycols are those having a molecular weight from about 300 to about 6000, e.g. polyethylene glycol 3350 and polyethylene glycol 4000. Preferred polyvinylpyrrolidone (PVP) compounds according to the invention are those having a molecular weight from about 7000 to about 54000, for instance PVP K12, K17, K25 and K30, in particular K12 and K17, PVP K17 being the most preferred. According to a preferred embodiment of the invention, the pharmaceutical aqueous suspension formulation of the invention in addition contain a suitable amount of a PVP compound, in particular K12 or K17, especially K17.

Suitable thickening or viscosity agents are for instance well known cellulose derivatives (e.g. methylcellulose, carboxymethylcellulose, hydroxyethylcellulose and hydroxypropylmethylcellulose), gelatin and acacia, in particular methylcellulose.

In addition, the formulations of the present invention may also include metal chelating agents, antioxidants or thiol-containing compounds and preservatives.

Suitable metal chelating agents are for instance ethylenediamine-tetracetic acid salts (e.g. edetate disodium).

Suitable antioxidants are for instance ascorbic acid derivatives (e.g. ascorbic acid, erythorbic acid, sodium ascorbate), thiol derivatives (e.g. thioglycerol, cysteine, acetylcysteine, cystine, dithioerythreitol, dithiothreitol, gluthathione), tocopherols, butylated hydroxyanisole, butylated hydroxytoluene, sulfurous acid salts (e.g. sodium sulfate, sodium bisulfite, acetone sodium bisulfite, sodium metabisulfite, sodium sulfite, sodium formaldehyde sulfoxylate, sodium thiosulfate) and nordihydroguaiareticacid.

Suitable preservatives are for instance phenol, chlorobutanol, benzylalcohol, methyl paraben, propyl paraben, benzalkonium chloride and cetylpyridinium chloride.

In addition, the formulations of the present invention may also include tonicity-adjusting agents. Suitable tonicity adjusting agents are for instance sodium chloride, sodium sulfate, dextrose, mannitol and glycerol.

The formulations of the present invention may also have a nitrogen blanket overlay on the head-space of the vial. Additionally, the formulations of the present invention may include purging the formulation buffer with helium, argon, or nitrogen.

When the formulation of the invention, besides L-Methionine, contains also buffering agents, useful buffers include e.g. those derived from acetic, aconitic, citric, glutaric, lactic, malic, succinic, phosphate and carbonic acids, as known in the art. Typically employed is an alkali or alkaline earth salt of one of the aforementioned acids. Phosphate and citrate buffers, such as phosphoric acid or a pharmaceutically acceptable salt thereof, or citric acid or a pharmaceutically acceptable salt thereof, are preferred. Sodium phosphate or sodium citrate is the preferred buffering agents, with sodium phosphate being most preferred.

The pharmaceutical aqueous suspension according to the invention is e.g. for intramuscular, subcutaneous and intradermal administration, preferably for intramuscular and subcutaneous administration.

A biological active compound according to the invention is any compound that after administration to a mammal, including humans, provides a therapeutic effect. Preferably it is a steroidal biologically active compound.

A steroidal biologically active compound according to the invention is the steroidal compound itself or, when appropriate, a pharmaceutically acceptable salt thereof as known in the art, e.g. medroxyprogesterone acetate, exemestane, estradiol cypionate, methylprednisolone acetate, oxabolone cypionate, clostebol acetate, testosterone cypionate; preferably medroxyprogesterone acetate, estradiol cypionate and exemestane, or a combination of two or more thereof according to the art.

Concentrations of medroxyprogesterone acetate in the formulation can range from about 1% w/v to about 40% w/v, preferably from about 3% w/v to about 30% w/v.

Concentrations of estradiol cypionate in the formulation can range from about 0.1% w/v to about 5% w/v, preferably from about 0.25% w/v to about 2.5 % w/v.

When a combination of estradiol cypionate and medroxyprogesterone acetate is the active ingredient of the pharmaceutical preparation of the invention, the amounts of such compounds present in the pharmaceutical preparation are substantially as here above.

Concentrations of exemestane in the formulation can range from about 1% w/v to about 25% w/v, preferably from about 5% w/v to about 20% w/v.

The steroidal biologically active compound is preferably in milled or micronized form according to the common practice.

The pH controlling activity of L-Methionine either alone or in combination with a conventional buffer is shown for instance by the following examples.

EXAMPLE 1 pH stabilization of a parenteral aqueous suspension of Exemestane (CAS: 6-Methylenandrosta-1,4-diene-3,17-dione; other name: Androsta-1,4-diene-3,17-dione-6-methylene) by means of L-Methionine.

Exemestane is an irreversible aromatase inhibitor, structurally related to the natural steroid androstenedione and it is a molecule prone to oxidation. When performing an experimental study, by adding different antioxidants to a 10% Exemestane parenteral aqueous suspension we have surprisingly found out that L-Methionine can stabilize the pH of the suspension. In fact, the experimental data provided in Table 3 clearly demonstrate that in the suspension formulation containing L-Methionine the pH reduction is minimized in comparison with the "as is" and that by adding L-Methionine, the pH of the suspension is stabilized at values above pH 4.5 even after 2 months storage at 55° C.

What is outmost surprising is that among the added antioxidants, only Methionine is effective in substantially controlling/stabilizing the pH of the suspension (after 2 months storage at 55° C. the pH decrease of the formulations containing ascorbic acid, and sodium metabisulfite is in fact comparable or worse than the one experimented in the "as is" formulation).

Therefore a simple antioxidant effect cannot explain the result obtained and the presence of a specific stabilizer, such as L-Methionine, is needed in order to prevent a dramatic pH decrease and stabilize the parenteral aqueous suspension.

The present invention, however, is not intended to be limited to any particular theory of the exact mechanism of this substantial pH stabilization but relates to the fact that a substantial pH stabilization is obtained, to the unconventional way through which this substantial pH stabilization is obtained and to its possible advantages.

It is an advantage of the present invention that the pH of these stabilized parenteral aqueous suspensions does not dramatically decrease during storage but, on the contrary, is maintained closer to the initial value (i.e. closer to neutrality) and therefore these stabilized suspensions can be safely administered without generating significant pain on patients.

TABLE 3 pH study of a 10% Exemestane parenteral aqueous suspension formulation containing different antioxidants.
Suspension composition (batch 13833/11): Exemestane 10%, methylparaben 0.18%, propylparaben 0.02%, sodium chloride 0.9%, PEG 4000 3.0%, polysorbate 80 0.2%, sodium hydroxide q.s. to pH 6.0–6.5 , WFI q.s to 100 ml.

|  | A: as is | B: +<br>Ascorbic<br>Acid | D: +<br>Sodium<br>Metabisulfite | E: +<br>L-Methionine |
|---|---|---|---|---|
| Time zero | 6.02 | 6.40 | 6.47 | 6.00 |
| 1 month at 55° C. | 4.28 | 4.20 | 2.30 | 4.86 |
| 2 months at 55° C. | 4.03 | 4.18 | 2.50 | 4.74 |

EXAMPLE 2 pH and technological quality (re-suspendability, syringeability) stabilization of a medroxyprogesterone acetate parenteral aqueous suspension by means of L-Methionine used alone or in combination with low and unconventional concentrations of phosphate buffer.

As previously shown in Table 2, the use of a conventional buffering agent, such as Phosphate buffer, in usual effective concentrations (approx. 1%) in order to stabilize the pH of a medroxyprogesterone acetate aqueous suspension has a detrimental effect on the suspension technological quality, i.e. resuspendability and syringeability.

In this example, outlined in Table 4 (Tables 4a and 4b), it is evident that the pH of the same type of suspension can be controlled/stabilized by using L-Methionine alone or by a combination of L-Methionine with a lower and unusual concentration of phosphate buffer (approx. 0.1%). In fact, when L-Methionine is used alone, as in the case of batch 13451/47-I, a substantially stabilized pH is obtained.

Besides, when L-Methionine is used in combination with a low unusual concentration of Phosphate buffer (approx. 0.1%) a synergistic effect is obtained.

In fact, as clearly shown in the case of batch 13451/47-C, when an unusually low concentration of phosphate buffer (approx. 0.1%) is used, no significant pH stabilization is obtained vs. the "as is" formulation.

On the contrary, when the same low unusual concentration of phosphate buffer (approx. 0.1%) is used in combination with L-Methionine, as in the case of batch 13451/84-D, a surprising super-additive effect is obtained in controlling/stabilizing the pH of the formulation.

Besides, when L-Methionine is used alone or in combination with a low unusual amount of phosphate buffer, no negative effect is produced on the suspension's technological quality, thus allowing the achievement of a pH stabilized medroxyprogesterone acetate suspension with good re-suspendability and syringeability properties that are maintained during storage.

On the contrary, when a usual effective concentration of phosphate buffer (approx. 1%) is used in order to stabilize the pH, as in the case of batch 13451/47-G, a detrimental effect on the physical stability of the formulation is obtained.

It is an advantage of this invention that the pH of parenteral aqueous suspensions can be substantially stabilized without using effective usual concentrations of conventional buffering agents, i.e. typically inorganic or organic acid salts, thus avoiding some substantial drawbacks, such as the profound effects caused by ionic species, and especially by polyvalent ions, on the nature and the stability of flocculated suspensions, with detrimental effects on suspension re-suspendability and syringeability.

TABLE 4 pH, resuspendability and syringeability study of a 20% Medroxyprogesterone Acetate (MPA) parenteral aqueous suspension formulated with different amounts of L-Methionine and Phosphate buffers.
Suspension composition:

Medroxyprogesterone Acetate 20%, MyristylGammaPicoliniumChloride 0.1% (batch 13451/84) or 0.2% (batch 13451/47), sodium sulphate 1.1%, PEG 3350 2.03%, sodium hydroxide q.s. to pH 6.5 , WFI q.s to 100 ml.

|  | 13451/47-A as is | 13451/47-C Phosphate ~ 0.1% (0.0066 M) | 13451/47-G Phosphate ~ 1% (0.066 M) | 13451/47-I L-Methionine 0.5% |
|---|---|---|---|---|
| pH |  |  |  |  |
| Time zero | 6.07 | 6.35 | 6.33 | 6.11 |
| 65° C.: 10 days | 2.85 | 3.03 | * | 5.29 |
| 65° C.: 15 days | 2.82 | 2.97 | * | 5.13 |
| 65° C.: 1 month | 2.88 | 3.06 | 5.13* | 4.76 |

TABLE 4-continued

|  | 13451/84-A as is | 13451/84-B L-Methionine 0.1% | 13451/84-C L-Methionine 0.25% | 13451/84-D L-Methionine 0.1% + Phosphate ~ 0.1% (0.0066 M) |
|---|---|---|---|---|
| PH |  |  |  |  |
| Time zero | 6.10 | 6.04 | 5.94 | 6.31 |
| 65° C.: 10 days | 3.00 | 4.49 | 5.28 | 5.92 |
| 65° C.: 15 days | 2.89 | 4.30 | 4.88 | 6.25 |
| 65° C.: 1 month | 3.01 | 3.83 | 4.55 | 6.20 |
| Resuspendability |  |  |  |  |
| 65° C.: 1 month | resuspendable (15s) | resuspendable (13s) | resuspendable (15s) | Resuspendable (14s) |
| Syringeability |  |  |  |  |
| 65° C.: 1 month | meets test | meets test | meets test | Meets test |
| Phosphate Buffers (M = molar) | approx. 0.1% | | approx. 1% | |
| Monobasic Sodium Phosphate · 1 H2O (MW 137.99) | mg 69.4/100 ml (0.005 M) | | mg 694/100 ml (0.05 M) | |
| Dibasic Sodium Phosphate · 12 H2O (MW 358.14) | mg 58.8/100 ml (0.0016 M) | | mg 588/100 ml (0.016 M) | |

* not resuspendable by manual wrist shaking, pH measured after mixing the suspension with a spatula
Resuspendability: In brackets the time of manual wrist shaking requested in order to obtain a homogeneous suspension (s = seconds).

EXAMPLE 3 pH stabilization of a medroxyprogesterone acetate and estradiol cypionate parenteral aqueous suspension by means of L-Methionine used alone or in combination with unconventional low amounts of phosphate buffer.

Estradiol cypionate and medroxyprogesterone acetate is an estro-progestinic combination that is used in contraception. Both estradiol cypionate and medroxyprogesterone acetate are quite stable molecules and no relevant degradation is reported when the two actives are formulated as a parenteral aqueous suspension. In fact, no particular stabilizers are requested to chemically stabilize the two active ingredients molecules, being the only issue to be solved is their hydrophobicity and therefore the need to use suitable wetting/suspending agents in order to obtain a re-suspendable and syringeable suspension. In the experimental trial reported in Table 5, a 1% estradiol cypionate and 5% medroxyprogesterone acetate parenteral aqueous suspension, containing suitable wetting/suspending agents has been formulated with different amounts of L-Methionine and with a combination of L-Methionine and a low and unusual concentration (approx. 0.1%) of Phosphate buffer. From the data obtained, not only L-Methionine "per se" is capable to prevent the relevant pH decrease occourring to the "as is" formulation and to maintain the pH of the formulation well above 4.5 even after 1 month storage at 65° C., but, most surprisingly, when used in combination with an lower and unconventional amount of phosphate buffer (approx. 0.1% or 0.0066M), the pH is stabilized to values close to the time zero value. Besides, the stabilizing effect is similar to the one obtained by buffering the formulation with a usual effective concentration (approx. 1% or 0.066M) of phosphate buffer.

It is an advantage of this invention that the pH of certain parenteral aqueous suspensions can be stabilized without buffering the formulation with a conventional buffering agents (i.e. inorganic/organic acid salts) or without usual effective concentrations of a conventional buffering agent.

As said before, the pH stabilized parenteral aqueous suspensions obtained by means of this invention do not contain conventional buffering agents or usual effective concentrations of buffering agents. As a consequence, a further advantage of this invention is that the so obtained parenteral aqueous suspensions do not have buffering capacity or significant buffering capacity per se, and therefore, when injected, the pH of the product can be more easily adjusted to the physiological value by the buffering capacity of the tissue fluids.

| -continued | |
|---|---|
| Monobasic Sodium Phosphate hydrate | 0.0694% |
| Dibasic Sodium Phosphate dodecahydrate | 0.0588% |
| L-Methionine | 0.150% |
| Sodium Hydroxide or Hydrochloric Acid | q.s. to PH 6.0–7.0 |
| Water for Injections | q.s. to 100 ml |

The excipients are dissolved in Water for Injections. The obtained vehicle is sterilized by steam sterilization or sterilant filtration. Sterile micronized medroxyprogesterone acetate is added to the vehicle, the obtained suspension is passed through a suitable homogenizer in aseptic condition and the pH is adjusted. The homogeneous suspension is then aseptically distributed in single-use containers.

The obtained product has desirable properties for parenteral use, keeps well and has a substantially stabilized pH.

TABLE 5 pH study of a 1% Estradiol Cypionate (ECP) and a 5% Medroxyprogesterone Acetate (MPA) parenteral aqueous suspension formulated with different amount of L-Methionine and Phosphate buffers. Suspension composition: MPA 5%, ECP 1%, methylparaben 0.18%, propylparaben 0.02%, sodium chloride 0.856%, PEG 3350 2.856%, polysorbate 80 0.19%, sodium hydroxide q.s. to pH 6.0–6.5, WFI q.s to 100 ml.

| Batch | 13510/01-A as is | 13510/01-B L-Methionine 0.5% | 13510/01-C L-Methionine 0.25% | 13510/01-D L-Methionine 0.1% | 13510/01-E Phosphate ~1% (0.066M) | 13510/01-F L-Methionine 0.1% + Phosphate ~1% (0.0066M) |
|---|---|---|---|---|---|---|
| pH | | | | | | |
| Time zero | 6.31 | 6.37 | 6.40 | 6.45 | 6.32 | 6.41 |
| 65° C.: 10 days | 4.49 | 5.71 | 5.62 | 5.54 | 6.26 | 6.21 |
| 65° C.: 15 days | 4.29 | 5.69 | 5.46 | 5.40 | 6.33 | 6.25 |
| 65° C.: 1 month | 3.91 | 4.73 | 4.67 | 4.62 | 6.29 | 5.98 |
| Phosphate Buffers (M = molar) | | | | | Approx. 0.1% | approx. 1% |
| Monobasic Sodium Phosphate.1 H2O (MW 137.99) | | | | | mg 69.4/100 ml (0.005M) | mg 694/100 ml (0.05M) |
| Dibasic Sodium Phosphate.12 H2O (MW 358.14) | | | | | mg 58.8/100 ml (0.0016M) | mg 588/100 ml (0.016M) |

The following are examples of pharmaceutical compositions according to the invention and are not intended to limit the scope of the invention itself.

EXAMPLE A

Stabilized Parenteral Aqueous Suspension of Medroxy Progesterone Acetate

The formulation is as ollows (% w/v):

| Medroxyprogesterone Acetate (micronized) | 20% |
|---|---|
| Myristyl Gamma Picolinium Chloride | 0.085% |
| Sodium Sulphate | 1.1% |
| Polyethytene Glycol 3350 | 2.03% |
| Polyvinylpyrrolidone K17 | 0.25% |

EXAMPLE B

Stabilized Parenteral Aqueous Suspension of Medroxy Progesterone Acetate

The formulation is as follows (% w/v):

| Medroxyprogesterone Acetate | 14% |
|---|---|
| Methylparaben | 0.18% |
| Propylparaben | 0.02% |
| Sodium Chloride | 0.8% |
| Polyethylene Glycol 3350 | 2.875% |
| Polysorbate 80 | 0.3% |
| Polyvinylpyrrolidone K17 | 0.5% |
| L-Methionine | 0.15% |
| Monobasic Sodium Phosphate hydrate | 0.0694% |
| Dibasic Sodium Phosphate dodecahydrate | 0.0588% |

-continued

| | |
|---|---|
| Sodium Hydroxide or Hydrochloric Acid | q.s. to PH 6.0–7.0 |
| Water for Injections | q.s. to 100 ml |

The manufacturing method includes preparation of a sterile vehicle, aseptic compounding of sterile micronized medroxyprogesterone Acetate into the vehicle and aseptic distribution of the obtained sterile homogenous suspension into single dose container.

The product has a substantially stabilized pH, good resuspendability and can be administered with a syringe-needle suitable for subcutaneous and intramuscular use.

EXAMPLE C
Stabilized Parenteral Aqueous Suspension of a Combination of Medroxyprogesterone
Acetate and Estradyol Cypionate.
The formulation is as follows (%w/v):

| | |
|---|---|
| Medroxyprogesterone Acetate (micronized) | 5% |
| Estradiol cypionate (micronized) | 1 |
| Methylparaben | 0.180% |
| Propylparaben | 0.020% |
| Sodium Chloride | 0.800% |
| Polyethylene Glycol 3350 | 2.856% |
| Polysorbate 80 | 0.190% |
| Polyvinylpyrrolidone K17 | 0.250% |
| L-Methionine | 0.150% |
| Monobasic Sodium Phosphate hydrate | 0.0694% |
| Dibasic Sodium Phosphate dodecahydrate | 0.0588% |
| Sodium Hydroxide or Hydrochloric Acid | q.s. to pH 6.0–7.0 |
| Water for Injections | q.s. to 100 ml |

The parabens are dissolved in Water for Injections previously heated at approximately 70–90° C. The parabens solution is cooled down to room temperature, the remaining excipients are added and dissolved and the pH is adjusted to the desired range.

Micronized medroxyprogesterone acetate and estradiol cypionate are slurried into the vehicle and the obtained dispersion is homogenized until a fine, syringeable suspension is obtained.

In order to obtain a sterile suspension suitable for parenteral administration sterile active drugs and vehicle are used and the obtained suspension aseptically distributed into single dose containers.

The obtained product can be easily resuspended and can easily flow though a syringe needle, has a substantially stabilized pH and is suitable for intradermal, subcutaneous and intramuscular administration.

EXAMPLE D
Stabilized Parenteral Aqueous Suspension of Exemestane
The formulation is as follows (% w/v):

| | |
|---|---|
| Exemestane (micronized) | 10% |
| Methylparaben | 0.18% |
| Propylparaben | 0.02% |
| Sodium Chloride | 0.83% |
| Polyethylene Glycol 4000 | 3.0% |
| Polysorbate 80 | 0.2% |
| Methylcellulose | 0.15% |
| Lecithin | 0.5% |
| L-Methionine | 0.1% |
| Edetate disodium | 0.05% |

-continued

| | |
|---|---|
| Monobasic Sodium Phosphate hydrate | 0.0694% |
| Dibasic Sodium Phosphate dodecahydrate | 0.0588% |
| Sodium Hydroxide or Hydrochloric Acid | q.s. to PH 6.0–7.0 |
| Water for Injections | q.s. to 100 ml |

Lecithin and methylcellulose are dispersed in approximately 20% of Water for Injections and the obtained dispersion autoclaved. The other excipients are dissolved in the remaining 80% of Water for Injections and the obtained solution sterilized by sterilant filtration. The two preparations are compounded in aseptic environment, the pH is adjusted and sterile exemestane is added.

The obtained suspension is passed though a suitable homogenizer until a fine, syringeable suspension is obtained and then aseptically distributed.

The product has desirable properties for parenteral use, keeps well and has a substantially stabilized pH.

What is claimed is:

1. A pharmaceutical aqueous suspension formulation for parenteral administration having substantially stabilized pH comprising a biologically active steroidal compound and a pH controlling effective concentration of L-Methionine.

2. A pharmaceutical formulation according to claim 1, wherein the pH controlling effective concentration of L-Methionine is from about 0.005% w/v or w/w to about 5% w/v or w/w.

3. A pharmaceutical composition according to claim 1, wherein the pH range of the formulation is from about pH3.0 to about pH8.0.

4. A pharmaceutical composition according to claim 3, wherein the biologically active steroidal compound is exemestane, medroxyprogesterone acetate or estradiol cypionate or a mixture of medroxyprogesterone acetate and estradiol cypionate.

5. A pharmaceutical aqueous suspension formulation for parenteral administration having substantially stabilized pH, comprising a biologically active steroidal compound, a buffering agent and L-Methionine in concentrations effective to produce a pH controlling superadditive effect.

6. A pharmaceutical composition according to claim 5, wherein the buffering agent is a phosphoric acid salt in a concentration lower than 0.4% w/v or w/w.

7. A pharmaceutical composition according to claim 6, wherein the concentration of the phosphoric acid salts is lower than 0.2% w/v or w/w.

8. A pharmaceutical composition according to claim 7 wherein the pH range of the formulation is from about pH 3.0 to about pH 8.0.

9. A pharmaceutical composition according to claim 1 wherein the biologically active steroidal compound is at least one compound selected from the group consisting of medroxyprogesterone acetate, exemestane, estradiol cypionate, methylprednisolone acetate, oxabolone cypionate, clostebol acetate and testosterone cypionate or a pharmaceutical acceptable salt thereof.

10. A pharmaceutical formulation according to claim 3 wherein the biologically active steroidal compound is medroxyprogesterone acetate.

11. A pharmaceutical formulation according to claim 3 wherein the biologically active steroidal compound is methylprednisolone acetate.

12. A pharmaceutical formulation according to claim 3 wherein the biologically active steroidal compound is exemestane.

13. A pharmaceutical formulation according to claim 3 wherein the biologically active steroidal compound is a mixture of medroxyprogesterone acetate and estradiol cypionate.

14. A pharmaceutical formulation according to claim 10 wherein the concentration of medroxyprogesterone acetate is about 1% w/v to about 40% w/v.

15. A pharmaceutical formulation according to claim 12 wherein the concentration of exemestane is about 1% w/v to about 25% w/v.

16. A pharmaceutical formulation according to claim 13 wherein the concentration of medroxyprogesterone acetate is from about 1% w/v to 40% w/v and the concentration of estradiol cypionate is from about 0.1% w/v to about 5% w/v.

17. A pharmaceutical formulation according to claim 1 containing at least one material selected from the group consisting of surfactants, suspending agents, thickening agents and density adjusting agents.

18. A pharmaceutical formulation according to claim 1 containing a preservative selected from the group consisting of phenol, chlorobutanol, benzylalcohol, methyl paraben, propyl paraben, benzalkonium chloride and cetylpyridinium chloride.

19. A pharmaceutical formulation according to claim 1 containing an antioxidant selected from the group consisting of ascorbic acid, erythorbic acid, sodium ascorbate, thioglycerol, cysteine, acetylcysteine, cystine, dithioerythreitol, dithiothreitol, gluthathione, tocopherols, butylated hydroxyanisole, butylated hydroxytoluene, sodium bisulfite, acetone sodium bisulfite, sodium metabisulfite, sodium sulfite, sodium formaldehyde sulfoxylate, sodium thiolsulfate and nordihydroguaiareticacid.

20. Process for the preparation of a pharmaceutical aqueous suspension formulation having substantially stabilized pH, for parenteral administration of a biologically active steroidal compound, comprising adding a pH controlling effective concentration of L-Methionine thereto.

21. A process for the preparation of a pharmaceutical aqueous suspension formulation having substantially stabilized pH, for parenteral administration of biologically active steroidal compound, comprising adding L-Methionine and a buffering agent thereto in concentrations effective to produce a pH controlling superadditive effect.

* * * * *